(12) United States Patent
Coffeen et al.

(10) Patent No.: US 7,306,361 B2
(45) Date of Patent: Dec. 11, 2007

(54) BONE CEMENT MIXING AND DELIVERY SYSTEM WITH MULTIPLE ADVANCEMENT MECHANISMS AND METHOD OF USE

(75) Inventors: Jared P Coffeen, Portage, MI (US); Richard F Huyser, Kalamazoo, MI (US); Christopher M Tague, Portage, MI (US); Weston Pernsteiner, Houghton, MI (US); Dennis A. Stratton, Plainwell, MI (US)

(73) Assignee: Stryker Corporation, Kalamazoo, MI (US)

( * ) Notice: Subject to any disclaimer, the term of this patent is extended or adjusted under 35 U.S.C. 154(b) by 9 days.

(21) Appl. No.: 11/349,621

(22) Filed: Feb. 8, 2006

(65) Prior Publication Data

US 2007/0041267 A1 Feb. 22, 2007

Related U.S. Application Data

(60) Continuation of application No. 10/801,748, filed on Mar. 16, 2004, now Pat. No. 7,134,782, which is a division of application No. 10/229,349, filed on Aug. 27, 2002, now Pat. No. 6,736,537, which is a continuation of application No. 09/981,552, filed on Oct. 17, 2001, now Pat. No. 6,547,432.

(60) Provisional application No. 60/325,783, filed on Jul. 16, 2001.

(51) Int. Cl.
*B01F 15/02* (2006.01)
*B01F 13/06* (2006.01)

(52) U.S. Cl. ............... 366/189; 366/139; 366/195; 366/255; 366/332

(58) Field of Classification Search ............... 366/189, 366/195, 194, 139, 255, 256, 332
See application file for complete search history.

(56) References Cited

U.S. PATENT DOCUMENTS

| | | | |
|---|---|---|---|
| 1,612,996 A | | 1/1927 | Waagbo |
| 3,144,966 A | | 8/1964 | Cook |
| 3,216,616 A | * | 11/1965 | Blankenship, Jr. ........... 222/47 |
| 3,217,946 A | | 11/1965 | Cook |
| 3,459,341 A | * | 8/1969 | Copeland .................... 222/386 |
| 4,010,934 A | | 3/1977 | McCord et al. |
| 4,197,967 A | | 4/1980 | Baur et al. |
| 4,208,133 A | | 6/1980 | Korte-Jungermann |
| 4,338,925 A | | 7/1982 | Miller |
| 4,371,094 A | | 2/1983 | Hutter, III |

(Continued)

*Primary Examiner*—Tony G. Soohoo
(74) *Attorney, Agent, or Firm*—Howard & Howard Attorneys, P.C.

(57) ABSTRACT

A bone cement mixing and delivery assembly is disclosed for mixing a powdered copolymer and a liquid monomer to form a bone cement and delivering the bone cement. The assembly includes a cartridge having a distal end and a proximal end and defining a mixing chamber between the distal end and the proximal end. A transfer mechanism having a cap and a stem supporting a piston and a plunger is connected to the distal end. The transfer mechanism includes a first advancement mechanism for advancing the piston and plunger in unison and a second advancement mechanism for moving the plunger independent of the piston. The assembly further includes a removable handle having a shaft for attachment of a mixing blade and a quick-release connector and a release button for locking and unlocking the mixing blade from the removable handle.

13 Claims, 11 Drawing Sheets

U.S. PATENT DOCUMENTS

| | | | | |
|---|---|---|---|---|
| 4,405,249 | A | 9/1983 | Scales | |
| 4,461,407 | A | 7/1984 | Finnegan | |
| 4,526,303 | A | 7/1985 | Harrod | |
| 4,546,767 | A | 10/1985 | Smith | |
| 4,547,076 | A | 10/1985 | Maurer | |
| 4,653,487 | A | 3/1987 | Maale | |
| 4,671,263 | A | 6/1987 | Draenert | |
| 4,676,406 | A | 6/1987 | Frischmann et al. | |
| 4,693,656 | A | 9/1987 | Guthrie | |
| 4,966,601 | A | 10/1990 | Draenert | |
| 4,994,065 | A | 2/1991 | Gibbs et al. | |
| 5,071,040 | A | 12/1991 | Laptewicz, Jr. | |
| 5,181,636 | A | 1/1993 | Anderson et al. | |
| 5,341,964 | A | 8/1994 | Medved | |
| 5,431,654 | A | 7/1995 | Nic | |
| 5,501,374 | A | 3/1996 | Laufer et al. | |
| 5,514,135 | A | 5/1996 | Earle | |
| 5,556,009 | A | 9/1996 | Motzko | |
| 5,638,997 | A | 6/1997 | Hawkins et al. | |
| 5,681,317 | A | 10/1997 | Caldarise | |
| 5,762,237 | A | 6/1998 | Chang | |
| 5,829,875 | A | 11/1998 | Hagel et al. | |
| 5,876,116 | A * | 3/1999 | Barker et al. | 366/182.3 |
| 5,893,488 | A | 4/1999 | Hoag et al. | |
| 5,961,211 | A * | 10/1999 | Barker et al. | 366/182.3 |
| 6,019,765 | A | 2/2000 | Thornhill et al. | |
| 6,033,105 | A * | 3/2000 | Barker et al. | 366/182.3 |
| 6,045,555 | A | 4/2000 | Smith et al. | |
| 6,048,346 | A | 4/2000 | Reiley et al. | |
| 6,083,229 | A | 7/2000 | Constantz et al. | |
| 6,086,594 | A | 7/2000 | Brown | |
| 6,149,655 | A | 11/2000 | Constantz et al. | |
| 6,155,463 | A | 12/2000 | Dentler | |
| 6,547,432 | B2 * | 4/2003 | Coffeen et al. | 366/130 |
| 6,736,537 | B2 * | 5/2004 | Coffeen et al. | 366/130 |
| 6,984,063 | B2 * | 1/2006 | Barker et al. | 366/139 |
| 7,029,163 | B2 * | 4/2006 | Barker et al. | 366/139 |
| 7,134,782 | B2 * | 11/2006 | Coffeen et al. | 366/242 |
| 2004/0174768 | A1 * | 9/2004 | Coffeen et al. | 366/139 |
| 2006/0028907 | A1 * | 2/2006 | Barker et al. | 366/139 |
| 2007/0041267 | A1 * | 2/2007 | Coffeen et al. | 366/189 |

* cited by examiner

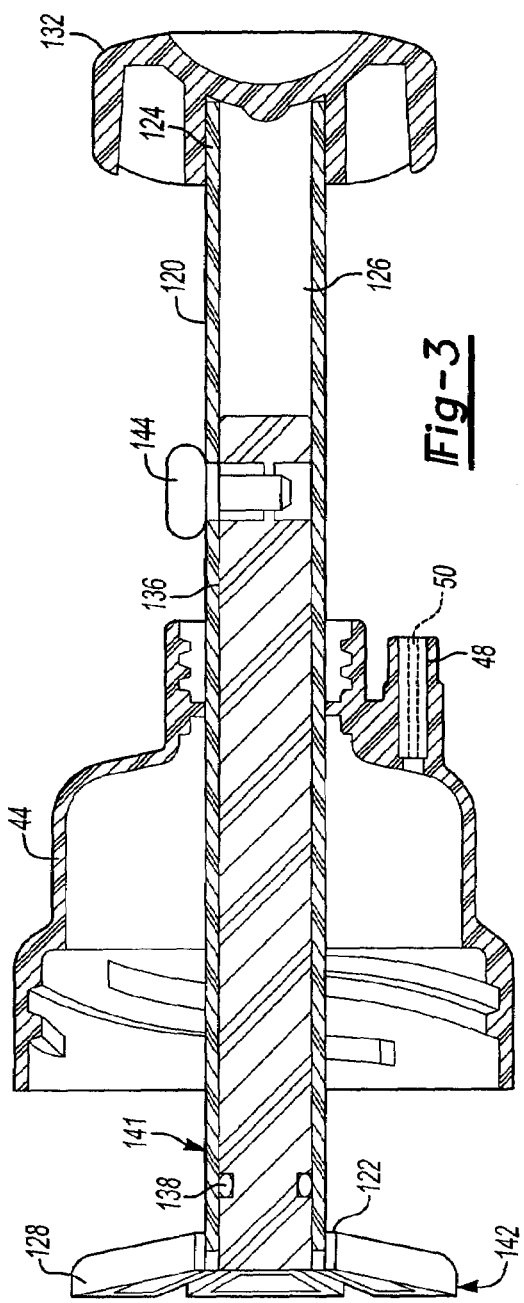
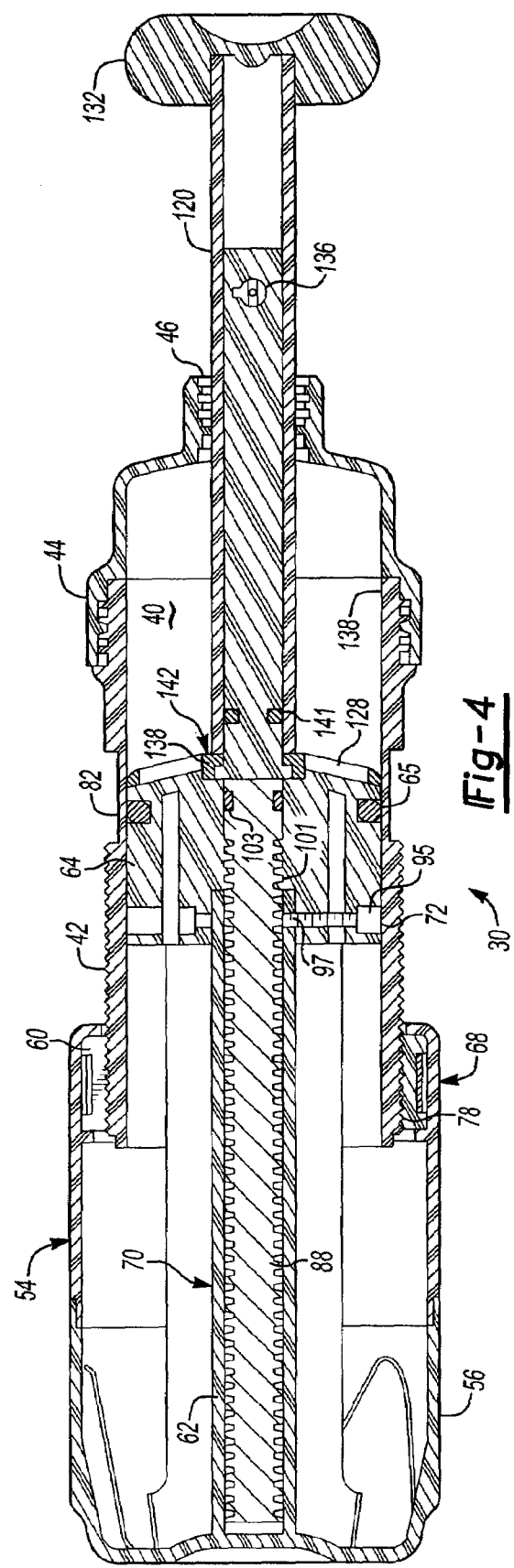

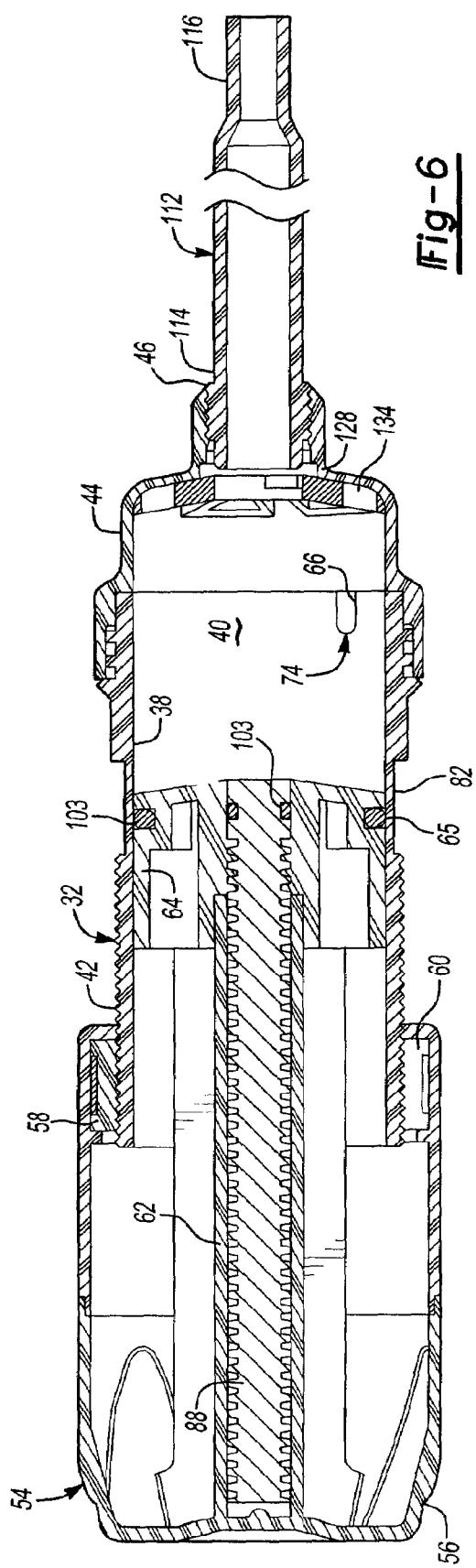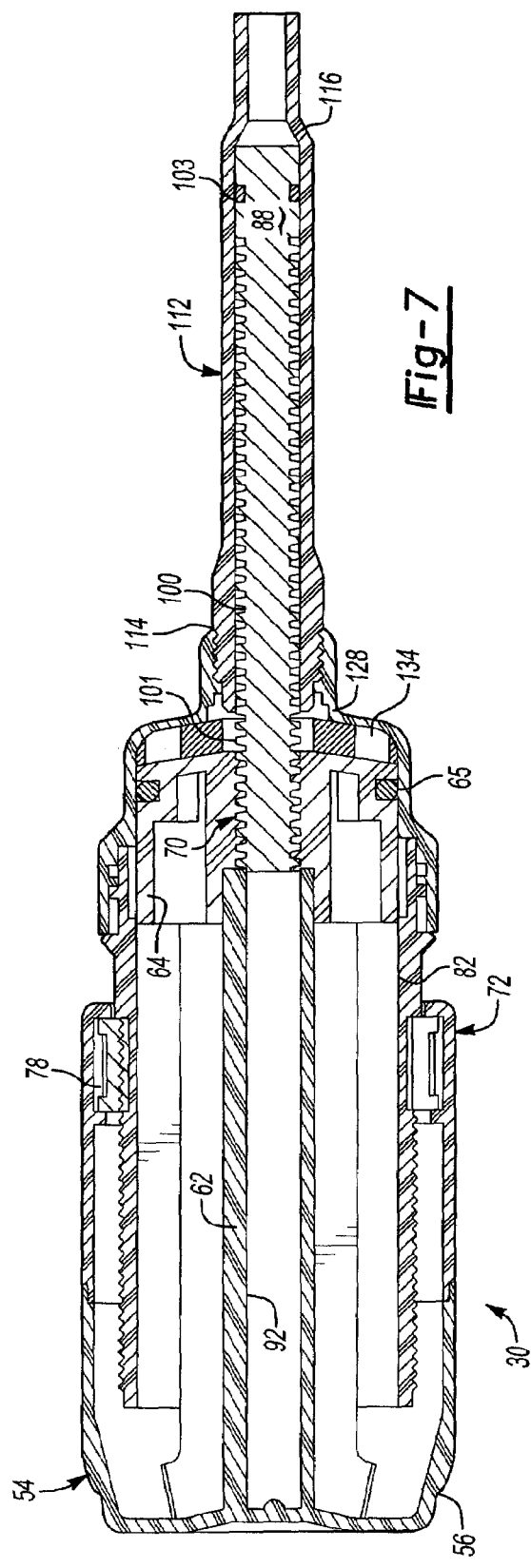

BONE CEMENT MIXING AND DELIVERY SYSTEM WITH MULTIPLE ADVANCEMENT MECHANISMS AND METHOD OF USE

This application is a continuation of U.S. patent application Ser. No. 10/801,748 filed Mar. 16, 2004, now U.S. Pat. No. 7,134,782, which is a divisional of U.S. patent application Ser. No. 10/229,349 filed Aug. 27, 2002, now U.S. Pat. No. 6,736,537, which is a continuation of U.S. patent application Ser. No. 09/981,552 filed Oct. 17, 2001, now U.S. Pat. No. 6,547,432 which claims priority to U.S. Provisional Patent Application Ser. No. 60/325,783 filed Jul. 16, 2001.

FIELD OF THE INVENTION

The present invention relates generally to a bone cement delivery assembly, one that is particularly suited for mixing a powdered copolymer and a liquid monomer to form a bone cement and delivering the bone cement.

BACKGROUND OF THE INVENTION

In many surgical procedures, particularly orthopedic procedures, it is common practice to affix a prosthesis to a bone or joint structure for improving the strength, rigidity and movement of the bone/joint structure. Such prosthetic devices have been widely used, hip joints and knee joints are the most common examples of areas where prosthetic devices are used to reduce or eliminate pain and suffering that exists from typical leg movements.

As part of these surgical procedures, it has become common practice to secure the prosthesis to the bone or joint using a cement formed by mixing a polymer powder and a liquid monomer. The two components must be thoroughly blended together to achieve the required consistency for the fully mixed cement. The fully mixed cement is then loaded into a separate dispensing apparatus for placement in the desired area and affixing of the prosthesis to the desired site.

Other uses of bone cement include repairing or mending bone fractures or shattered bone occurring from extreme trauma. Bone cement may also be used during cosmetic or dental surgery. Moreover, bone cement may be used as a drug delivery or release system, whereby the bone cement is mixed with antibiotics or other desired drugs and applied to a specific surgical site such that the drugs leach out and are delivered directly to the surgical site. Some bone cements are also designed to be absorbed by the body over time.

Because of the necessity for a fairly quick setting material, the cement is almost universally prepared by a surgical assistant during the course of the operation in the sterile operating room. Conventional bone cements are generally polymeric materials which are prepared by copolymerization of the components as needed. Bone cement is prepared by copolymerizng the liquid monomer and the powdered copolymer, such as methyl methacrylate and polymethyl methacrylate or methyl methacrylate styrene. In order to provide a bone cement having the desired properties, the compounds must be uniformly and thoroughly mixed so that a homogeneous reaction product is produced.

During the mixing and subsequent chemical reaction various vapors are produced. Due to the noxious and toxic nature of such vapors, it is highly undesirable to be exposed to them, particularly for extended periods of time in the course of multiple preparations. Since it is necessary that the mixing be carried out for extended periods of time to ensure a uniform reaction product and a minimum of concentration of volatile reactants, the period of exposure to harmful vapors can be substantial. Moreover, during the mixing of the constituent components of the cement, air bubbles may be formed within the cement.

Most often, the two components forming the cement are mixed in a mixing vessel and, once fully mixed, the cement is manually transferred from the mixing vessel to a dispensing member of a dispensing device. Typically, devices similar to caulking guns are employed for dispensing the fully mixed cement to the desired location in the patient. These devices have a piston which allows the bone cement to remain in the dispensing member.

In some other prior art systems, the cement is mixed in one vessel which is then directly connected to a feeding system that enables the mixed cement to be added to a holding tube for use with the dispensing device. The dispensing system, however, is separate and exposes the mixed cement to the surrounding personnel. Furthermore, care must be exercised during the transfer of the mixed cement to the dispenser to avoid introducing air into the cement or to avoid dropping, spilling, or contaminating the cement.

Other prior art systems utilize a handle that operates mixing paddles in a closed cylinder for combining the cement constituents. Upon mixing the bone cement, the handle must be removed. Conventional systems incorporate frangible handles that when broken may produce fragments that could contaminate the bone cement.

One such device is disclosed in U.S. Pat. No. 5,551,778 to Hauke et al. The '778 patent discloses a device having a mixing cylinder and a mixing plunger extending therethrough. The standard powder and liquid components are introduced into the chamber to form a bone cement and the mixing plunger mixes the two components. The mixing plunger has a predetermined break point for breaking the mixing plunger and allowing for its removal from the mixing cylinder. A discharge nozzle is then connected to the mixing cylinder and the mixing chamber is connected to a drive mechanism. The drive mechanism includes a discharge plunger that is passed through the mixing cylinder forcing the bone cement from the mixing cylinder out the nozzle. A portion of the bone cement remains in the discharge nozzle and thus the system does not ensure complete delivery of the bone cement into the patient.

Another such device is disclosed in U.S. Pat. No. 5,879,116 to Barker et al. The '116 patent discloses a device having a mixing chamber integral with a delivery chamber. The bone cement components are introduced into the mixing chamber and a paddle having a handle extending from the mixing chamber is utilized to mix the components and form the bone cement. Once the components are adequately mixed, a passage way is opened between the mixing chamber and the delivery chamber. The handle is actuated causing rotation of the paddle and of an auger disposed within the delivery chamber. The paddle transfers the bone cement from the mixing chamber to the auger. The auger has threads, which taper away from the mixing chamber for pulling the bone cement from the mixing chamber into the delivery chamber. One disadvantage of this system is that the bone cement must have a relatively low viscosity to be pulled by the auger into the delivery chamber. Additionally, the bone cement may remain on the walls of the mixing chamber where the paddle is unable to reach it.

Accordingly, it would be advantageous to provide a bone cement mixing and delivery assembly that includes a mechanism to transfer all of the bone cement from a mixing chamber to an delivery cartridge and to deliver all of the bone cement from the delivery cartridge into the patient.

SUMMARY OF THE INVENTION AND ADVANTAGES

The present invention provides a bone cement mixing and delivery assembly for mixing a powdered copolymer and a liquid monomer to form a bone cement and delivering the bone cement. The device includes a cartridge having a distal end and a proximal end defining a mixing chamber between the distal end and the proximal end. A lid is connected to the proximal end and has an aperture. A transfer mechanism is connected to the distal end and in sealing engagement with the cartridge. A piston is connected to the transfer mechanism such that movement of the transfer mechanism extends the piston through the mixing chamber for transferring the bone cement from the mixing chamber to the proximal end. The device is characterized by a plunger extending from the piston for forcing the bone cement through the aperture and delivering the bone cement to the patient.

Accordingly, the subject invention proves a method comprising the steps of filling a chamber having a proximal end with the bone cement, advancing a piston and a plunger in unison within the chamber for transferring the bone cement out of an aperture in the proximal end of the chamber, and the method is characterized by advancing the plunger independently of the piston to extend the plunger beyond the piston and into the aperture.

The subject invention provides many advantages over conventional systems. First, the bone cement is mixed and dispensed from the same container, thus eliminating the need to manually transfer the bone cement from a mixing vessel to a dispensing device. In addition, the removable handle is released rather than broken off. Thus, cost is reduced, handling is minimized and the introduction of contaminants into the mixture is minimized or eliminated. Furthermore, the compound is not exposed to air, thereby reducing or eliminating exposure of noxious and toxic vapors to surrounding personnel during the surgical operation. Another advantage of the subject invention is that the compound is mixed in an environment evacuated by a vacuum. Thus, the formation of air bubbles is minimized, providing a uniform reaction product and, in turn, producing a stronger bone cement compound.

Additionally, the device of the subject invention provides a mechanism for transferring all of the bone cement from the mixing chamber to the patient.

BRIEF DESCRIPTION OF THE DRAWINGS

Other advantages of the present invention will be readily appreciated as the same becomes better understood by reference to the following detailed description when considered in connection with the accompanying drawings wherein:

FIG. 3 is a cross-sectional view of a lid with an aperture having the removable handle extending therethrough designed according to the present invention;

FIG. 4 is a cross-sectional view of the embodiment of FIG. 1 shown in a mixing phase;

FIG. 6 is a cross-sectional view of the embodiment of FIG. 1 shown at the start of the transfer stage;

FIG. 7 is a cross-sectional view of the embodiment of FIG. 1 shown after complete delivery of the bone cement;

DETAILED DESCRIPTION OF THE INVENTION

Referring to the Figures, wherein like numerals indicate like or corresponding parts throughout the several views, a bone cement mixing and delivery assembly for mixing a powdered copolymer and a liquid monomer to form a bone cement and delivering the bone cement is shown generally at 30. In one embodiment, delivery of the bone cement is performed percutaneously. Percutaneous, as used in the medical field, relates to passing or effectuating the bone cement through the skin. The mixing and delivery assembly 30 functions in three phases comprising a mixing phase, a transfer phase, and a delivery phase. All phases are described in detail below with the transfer and delivery phases described first, followed by the mixing phase. Specifically, FIGS. 5-7 and FIGS. 17-21 show the assembly 30 during the transfer and delivery phases. FIGS. 1-4 illustrate the assembly 30 during the mixing phase.

Figure 13:
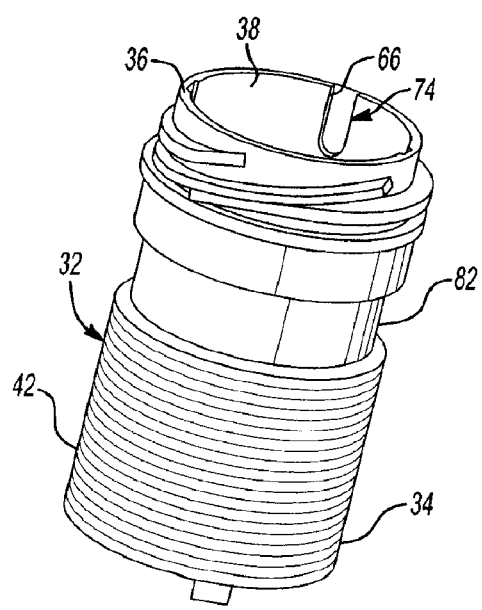
FIG. 13 is a perspective view of a cartridge designed according to the present invention.
Figure 14:
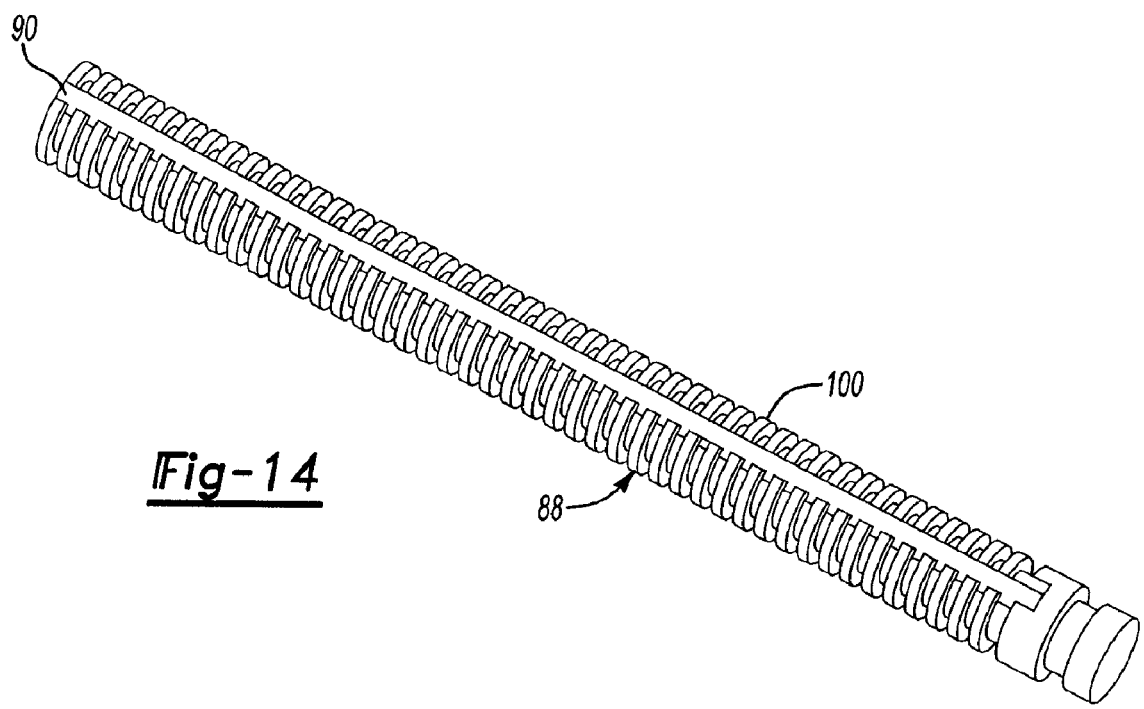
FIG. 14 is a perspective view of a plunger designed according to the present invention.

The mixing and delivery assembly 30 includes a cartridge 32 (shown separately in FIG. 13) having a distal end 34 and a proximal end 36 and defining a chamber 38 between the distal end 34 and the proximal end 36, as shown in FIGS. 4, 6, and 13. An external portion of the cartridge 32 adjacent the distal end 34 further includes male threads 42. In the preferred embodiment, the chamber 38 is a mixing chamber 40 for receiving the liquid monomer and the powdered copolymer to form the bone cement. The chamber 38 may, however, receive premixed bone cement, in which case the assembly 30 is used only to deliver the premixed bone cement to the patient. Alternatively, the chamber 38 may be packaged with the powdered copolymer. Thus, prior to use, only the liquid monomer is added.

A lid 44 is connected to the proximal end 36 and it has a first aperture 46. The lid 44 seatingly engages the proximal end 36. In the preferred embodiment, the lid 44 has threads for engaging corresponding threads on the proximal end 36 as shown in FIGS. 2-7. The lid 44 also has a vent 48 connected to the lid 44 for allowing a vacuum (not shown) to be attached to the vent 48 with a vacuum attachment 76 for removing gas particles from the chamber 38. The vacuum may be any device capable of applying a pressure differential, as is known in the art, for removing gas particles from the mixing chamber 40. Removal of the gas creates a stronger cement. Also the vacuum assists in the removal of obnoxious and potentially harmful gases produced during mixing. A filter 50 may also be disposed within the vent 48 for filtering the gas particles.

The mixing and delivery assembly 30 may further include a cooling chamber 52 positioned adjacent the mixing chamber 40 for receiving a cooling fluid (not shown) to cool the mixing chamber 40. The cooling chamber 52 is capable of receiving any cooling fluid as is known in the art. As the liquid monomer and powder copolymer are mixed, an exothermic chemical reaction occurs. Illustrative examples of such a cooling fluid include ice inserted into the cooling chamber 52 or chemicals which produce an endothermic reaction for cooling the chamber 38. Alternately, the cooling chamber 52 could be annular and connected to a cold air or water supply for passing cold air or water through the cooling chamber 52. The bone cement remains useable for a longer period of time if the heat from the exothermic reaction is dissipated.

Figure 9:
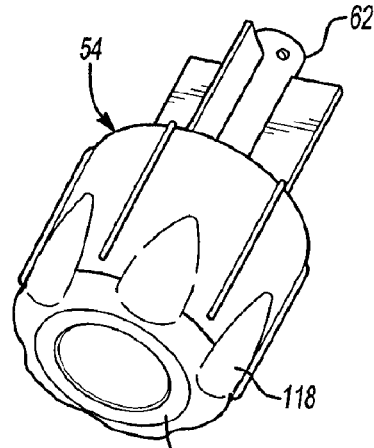
FIG. 9 is a perspective view of the transfer mechanism.
Figure 11:
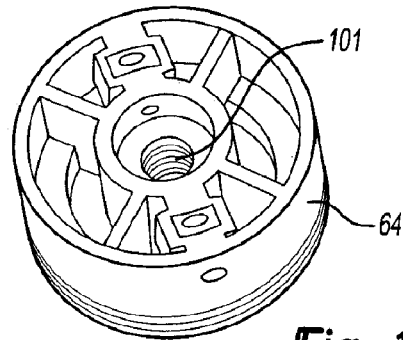
FIG. 11 is a bottom-side prespective view of a piston designed according to the present invention.
Figure 12:
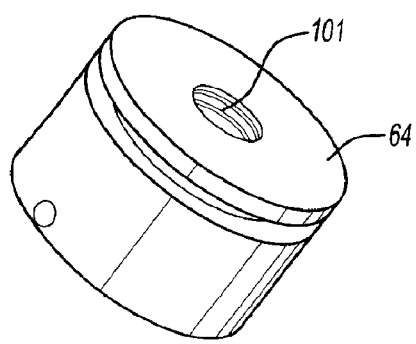
FIG. 12 is a top-side prespective view of the piston designed according to the present invention.

A transfer mechanism 54 threads onto the distal end 34, as shown in FIGS. 1, 2, 4-7, and 17-21. The transfer mechanism 54 includes a cap 56. The cap 56 has female threads 58 for engaging the male threads 42 of the distal end 34. The cap 56, as shown in FIG. 9, further includes a stem 62 extending from the cap 56. A piston 64 is rotatably supported by the stem 62 and housed within the cartridge 32. The piston 64 has a perimeter which extends to an inner wall of the chamber 38. The piston 64 is shown separately in FIGS. 11 and 12. The piston 64 also has a piston seal 65 between the piston 64 and the chamber 38 for preventing bone cement from flowing therebetween. Preferably, the piston seal 65 comprises an O-ring.

The transfer mechanism 54 has a first advancement mechanism 68 and a second advancement mechanism 70. The first advancement mechanism 54 is for use in the transfer phase to advance the piston 64 through the chamber 38 and transfer the bone cement from the chamber 38 and out the aperture 46. The first advancement mechanism 68 includes a pin system 72 interconnecting the piston 64 and the stem 62 for preventing rotation of the piston 64 relative to the stem 62 until the piston 64 reaches a stop position 74, shown in FIG. 6. The stop position 74 is defined by a channel 66 in the chamber 38 being adjacent the piston 64. The first advancement mechanism 68 further includes a disconnect system 78 disconnecting the female threads 58 from the male threads 42, as shown in FIG. 7. After the female threads 58 and the male threads 42 are disconnected, the cap 56 can be rotated relative to the cartridge 32 without moving or rotating the piston 64.

Figure 1:
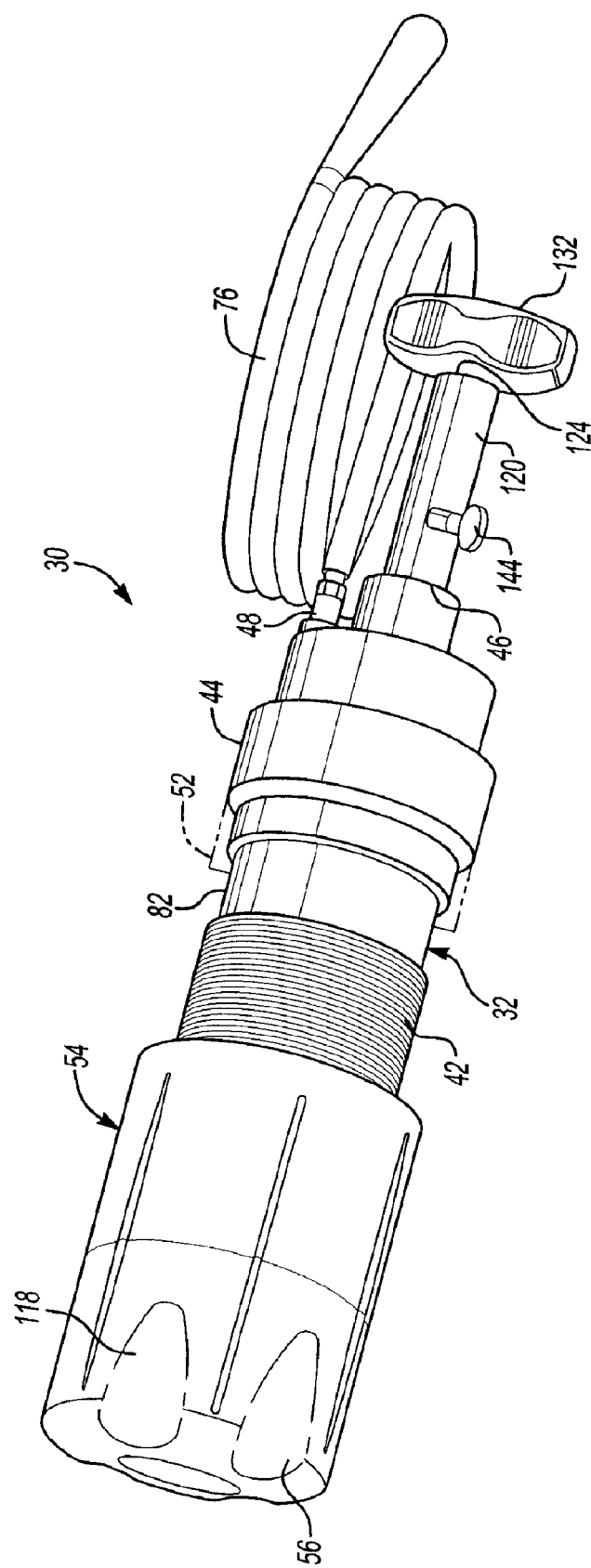
FIG. 1 is a perspective view of a first embodiment of a cement mixing and delivery assembly having a transfer mechanism and a removable handle designed according to the present invention.
Figure 2:
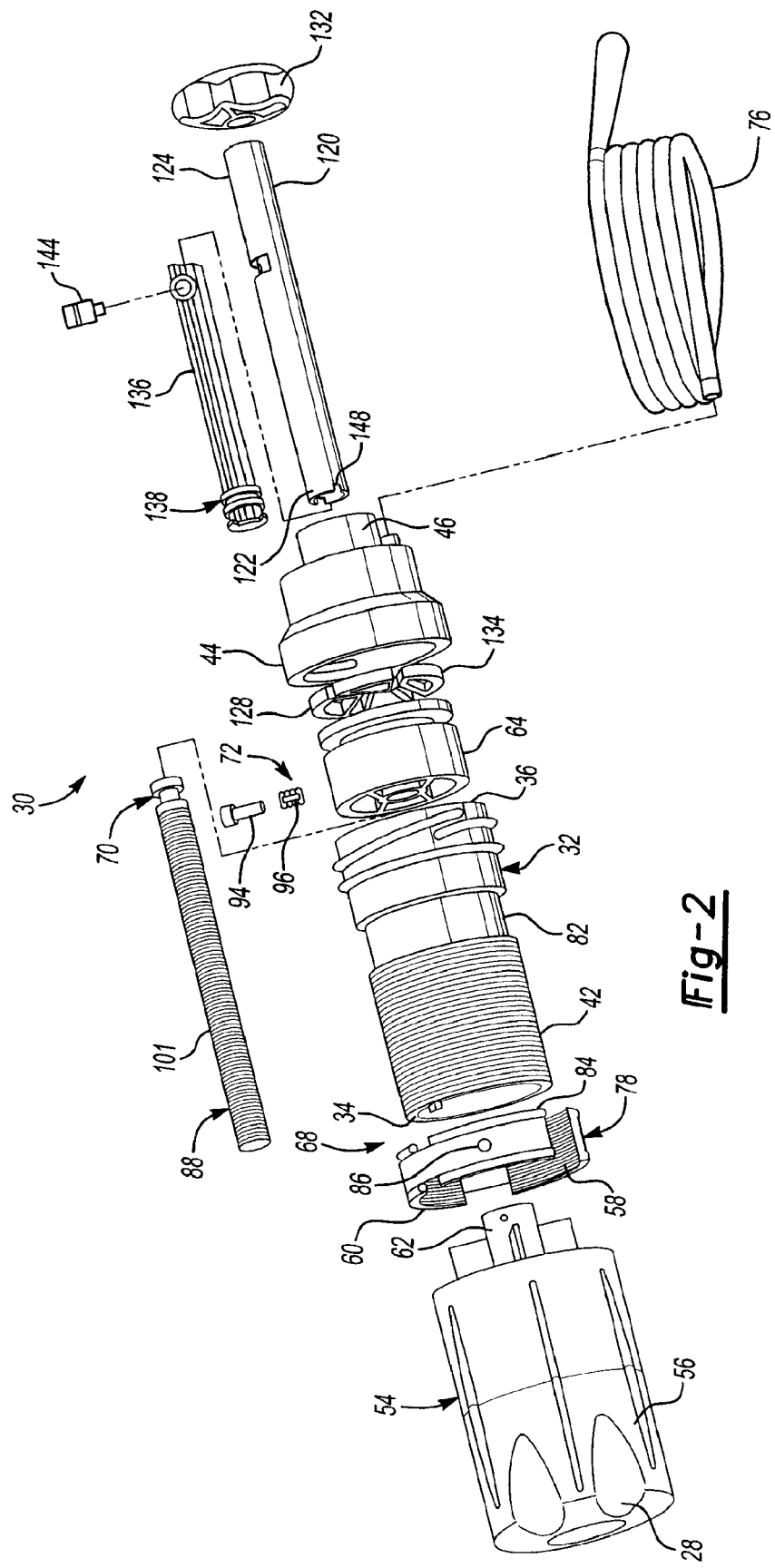
FIG. 2 is an exploded perspective view of the embodiment of FIG. 1.
Figure 5:
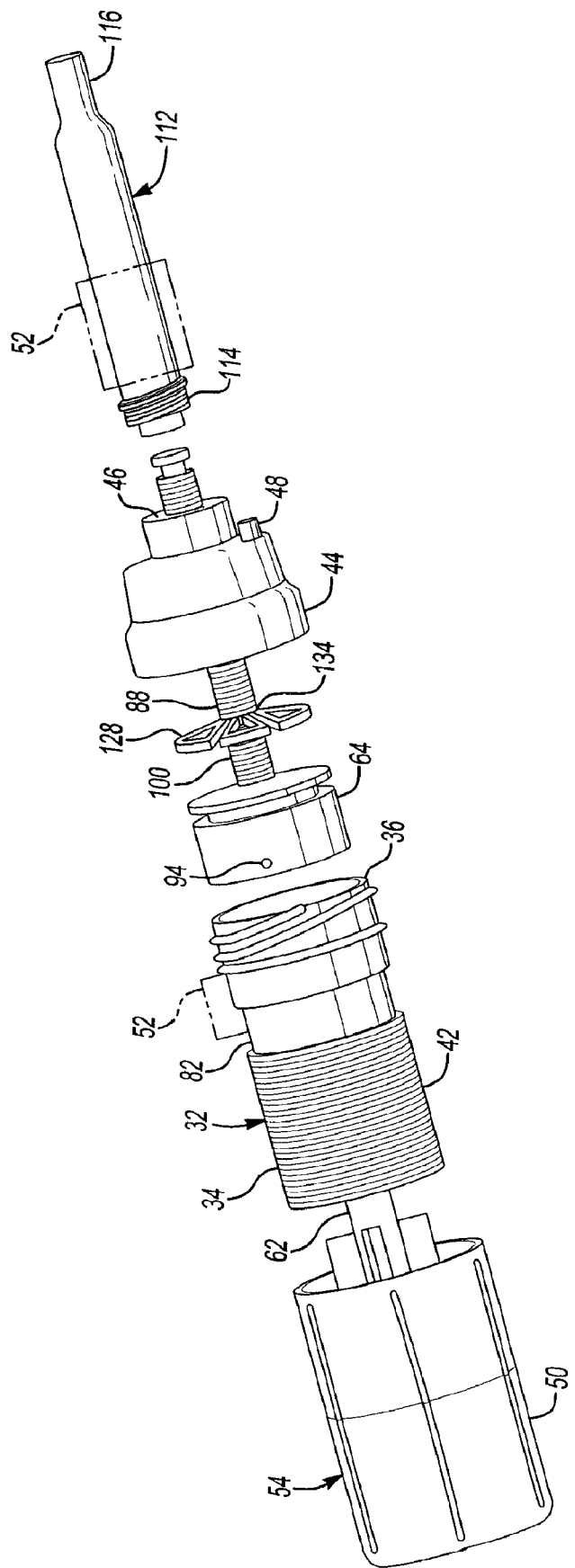
FIG. 5 is an exploded perspective view of the embodiment of FIG. 1 shown in a delivery phase.
Figure 8:
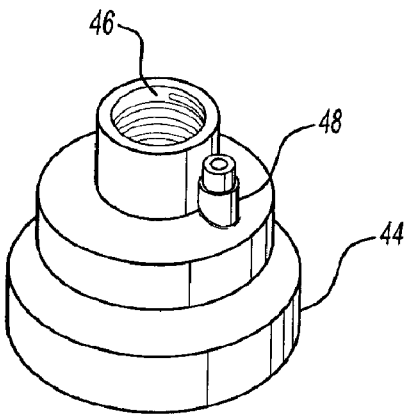
FIG. 8 is a perspective view of the lid.

In the preferred embodiment, the female threads 58 are formed as a plurality of circumferential segments 60. The plurality of circumferential segments 60 are connected to the transfer mechanism 54 to move axially along the male threads 42 thereby advancing the piston 64. The cartridge 32 includes an annular recess 82 adjacent the male threads 42. A first biasing device 84 moves the segments into the annular recess 82 once the piston 64 reaches the stop position 74. Preferably, the circumferential segments 60 are divided into sections and each section has a nipple 86 for engaging the first biasing device 84, as shown in FIG. 2. Additionally, the plurality of circumferential segments 60 may only encircle a portion of the threaded portion 40. Preferably, the first biasing device 84 is a metal spring band which collapses the plurality of circumferential segments 60 into the annular recess 82. As the circumferential segments 60 reach the end of the male threads 42, the first biasing device 84 forces the plurality of circumferential segments 60 into the annular recess 82. As the circumferential segments 60 are forced into the annular recess 82, the circumferential segments 60 disengage from the transfer mechanism 54 which disconnects from the piston 64. When the circumferential segments 60 have entered the annular recess 82, the transfer stage is completed and the bone cement has been transferred from the chamber 38 and out the aperture 46. The first biasing device 84 and the annular recess 82 prevent the first advancement mechanism 68 from being able to back down the threaded portion 42. In other words, the first biasing device 84 allows the mixing and delivery assembly 30 to be used for a single application.

The assembly 30 also includes a plunger 88 movable relative to the piston 64 for extending from the piston 64 and into the aperture 46 for forcing the bone cement through the aperture 46. The extending of the plunger 88 from the piston 64 through the aperture 46 is the beginning of the delivery phase. The plunger 88 has a groove 90 and the stem 62 has a tongue 92 for interconnecting the plunger 88 to the stem 62. The interconnection of the tongue 92 and the groove 90 allows the plunger 88 to rotate with the stem 62 and to move axially relative to the stem 62 in the delivery phase via threaded interaction between the plunger 88 and the piston 64.

The pin system 72 includes a pin 94 disposed radially to interconnect the stem 62 and the piston 64. The pin 94 has a head 95 and a tail 97 and the head 95 is larger than the tail 97. A second biasing device 96, comprising a spring around the tail 97, urges the pin 94 radially outwardly against the cartridge 32. The cartridge 32 has the channel 66 adjacent the proximal end 36 for receiving the head 95. As the first advancement mechanism 68 moves the piston 64 through the chamber 38, the spring is compressed due to the head 95 engaging the inner wall of the chamber 38. When the piston 64 reaches the stop position 74, the pin 94 is received by the channel 66 and the spring forces the pin 94 outward. Once this happens, the pin 94 no longer engages the stem 65 and only engages the chamber 38 and the piston 64.

The second advancement mechanism 70 includes threads 100 on the plunger 88 that engage threads 101 inside the piston 64. The second advancement mechanism 70 advances the plunger 88 from the piston 64 during the delivery phase. A plunger seal 103 is disposed between the plunger 88 and the piston 64 to prevent bone cement from flowing therebetween during the mixing and transfer phases. The tongue 92 and the groove 90 impart the continued rotation of the cap 56 to the plunger 88. The plunger 88 thereafter threadably engages the piston 64 such that the plunger 88 extends from the piston 64. Once the piston 64 has reached the stop position 74, the plunger 88 moves independently of the piston 64 and the piston 64 acts as a nut as the cap 56 is rotated.

Figure 17:
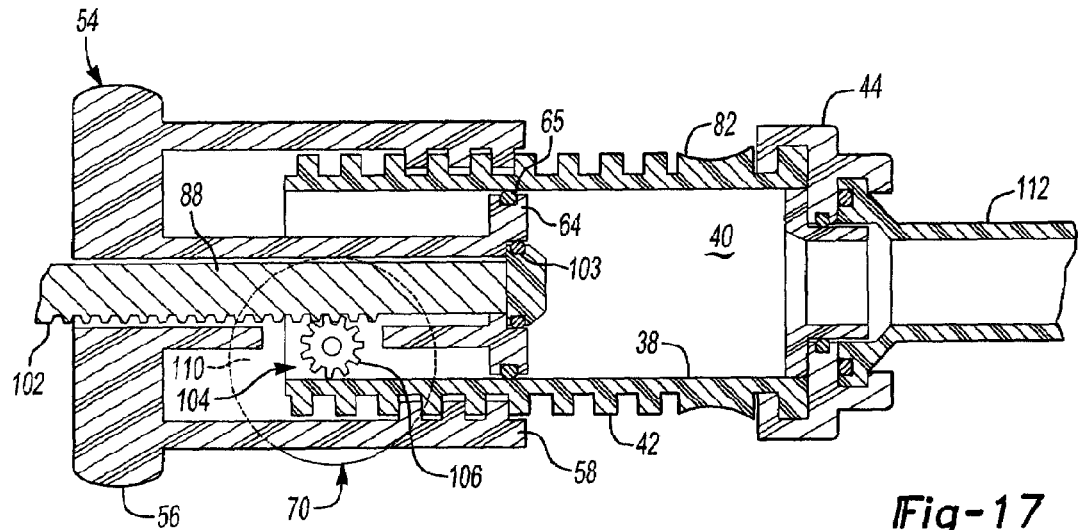
FIG. 17 is a cross-sectional view of a second embodiment of a cement mixing and delivery assembly designed according to the present invention.
Figure 18:
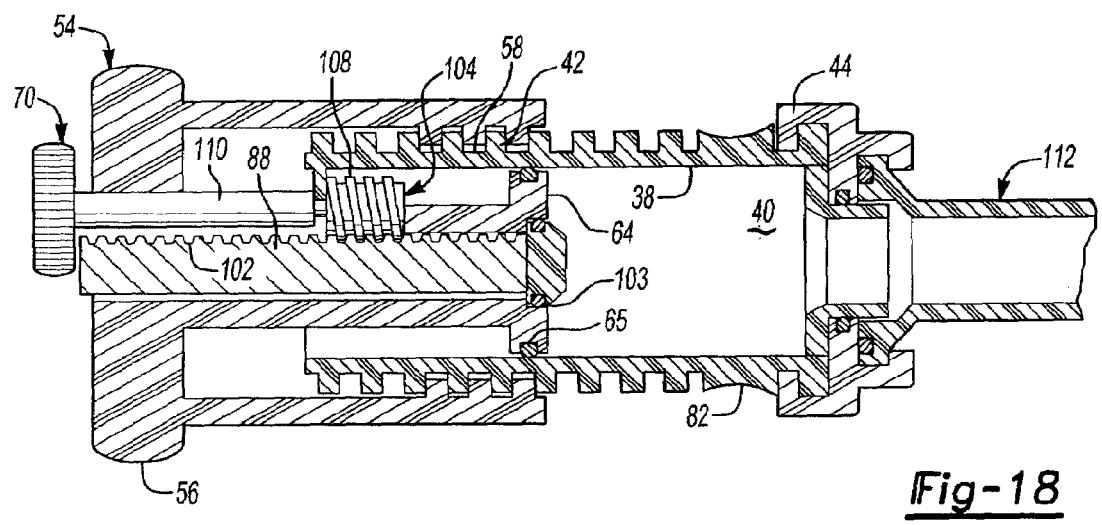
FIG. 18 is a cross-sectional view of a third embodiment of a cement mixing and delivery assembly designed according to the present invention.

Alternately, and as shown in FIGS. 17 and 18, the second advancement mechanism 70 may include a rack 102 connected to the plunger 88 and a gear 104 engaging the rack 102 to advance the plunger 88 during the delivery phase. The gear 104 may be either a pinion gear 106 (FIG. 17) or a worm gear 108 (FIG. 18). A rod 110 is connected to the gear 104 and extends through the transfer mechanism 54 for actuating the gear 104 manually or by a drive (not shown). The rod 110 is rotated causing the gear 104 to rotate causing the rack 102 to move linearly. Movement of the rack 102 extends the plunger 88 from the piston 64 and continues to deliver the bone cement through the aperture 46.

Figure 16:
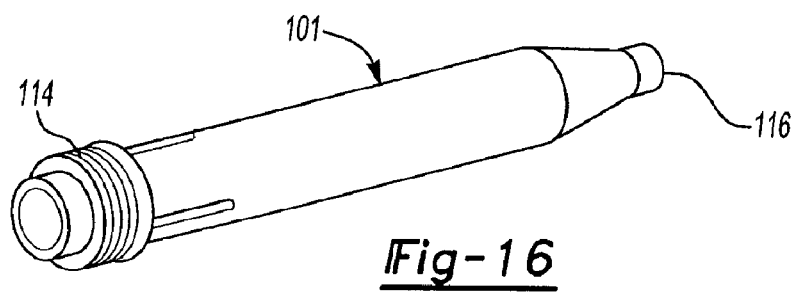
FIG. 16 is a perspective view of a delivery cartridge designed according to the present invention.

The assembly 30 further includes a delivery cartridge 112 having a cartridge end 114 connected to the aperture 46 of the lid 44 and extending to an open end 116. The delivery cartridge 112 (shown separately in FIG. 16) has a smaller diameter than the mixing chamber 40 and the plunger 88 has a smaller cross-section which allows the plunger 88 to extend through the aperture 46 and into the delivery cartridge 112. As the delivery cartridge 112 receives the plunger 88, the bone cement is forced through the delivery cartridge 112. The delivery cartridge 112 may also include cooling chambers 52 as discussed above for surrounding the mixing chamber 40. For example, a water-based gel may be inserted into the cooling chamber 52 around the delivery cartridge 112 and cooled. The cooled delivery cartridge 112 allows the bone cement to be available for use for longer periods of time. The delivery cartridge 112 may be permanently or removably connected to the lid 44. Alternate embodiments may have the delivery cartridge 112 connected to the opposite end of a removable handle 120.

Figure 19:
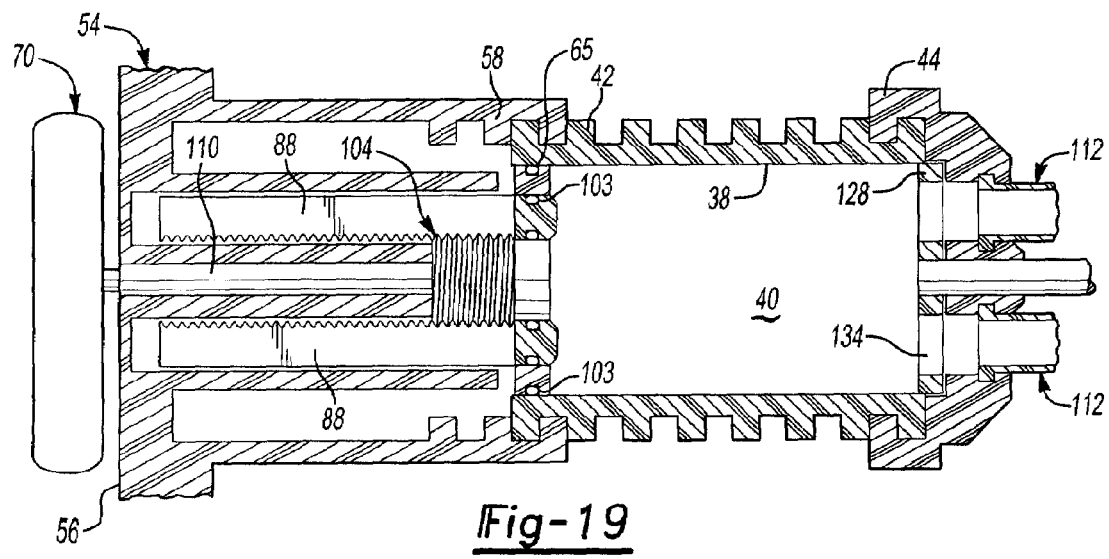
FIG. 19 is a cross-sectional view of a fourth embodiment of a cement mixing and delivery assembly having multiple plungers and designed according to the present invention.
Figure 20:
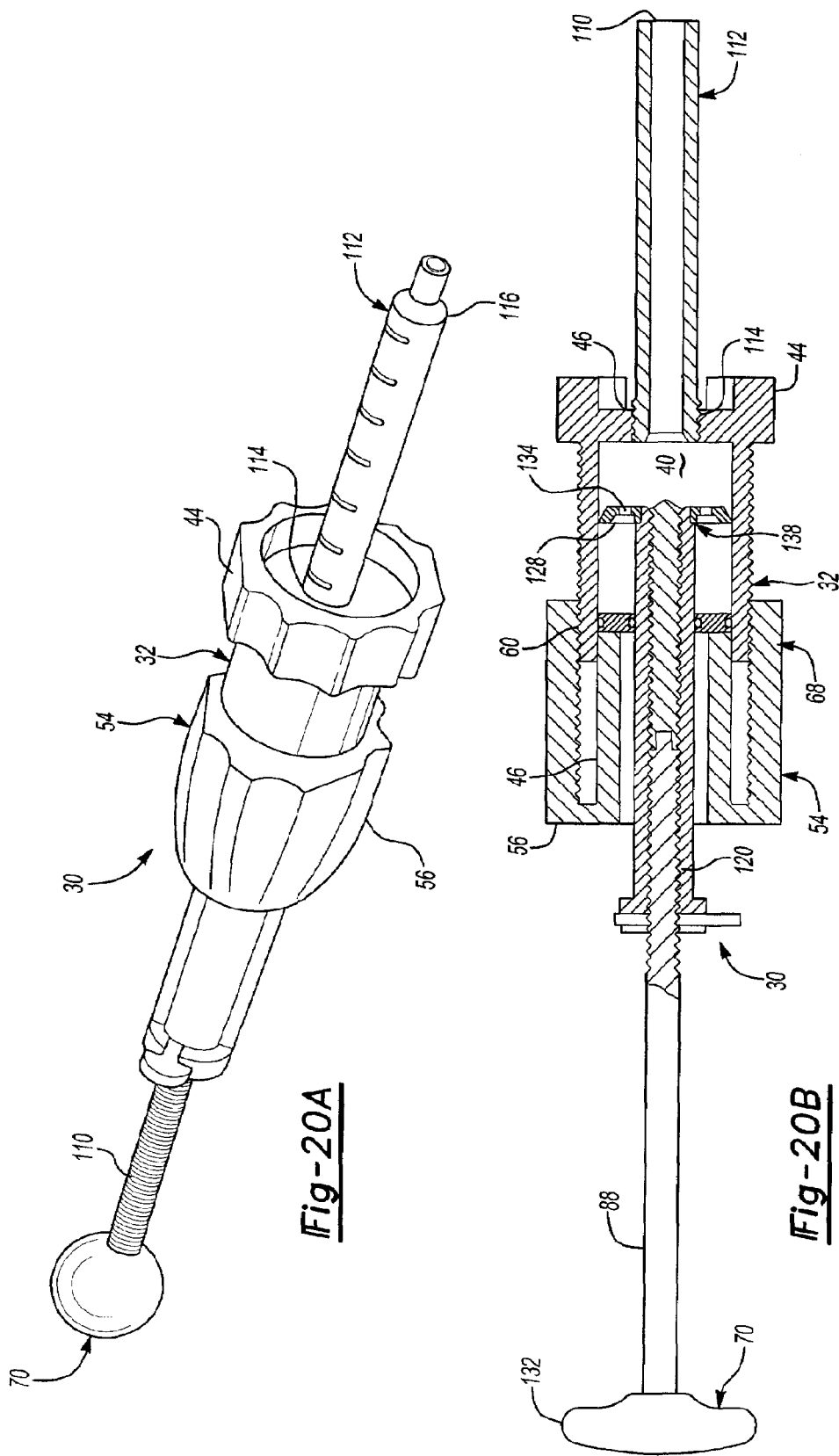
FIG. 20A is a perspective view of a fifth embodiment of a cement mixing and delivery device designed according to the present invention.
FIG. 20B is a cross-sectional view of the cement mixing and delivery device of FIG. 20A.
Figure 21:
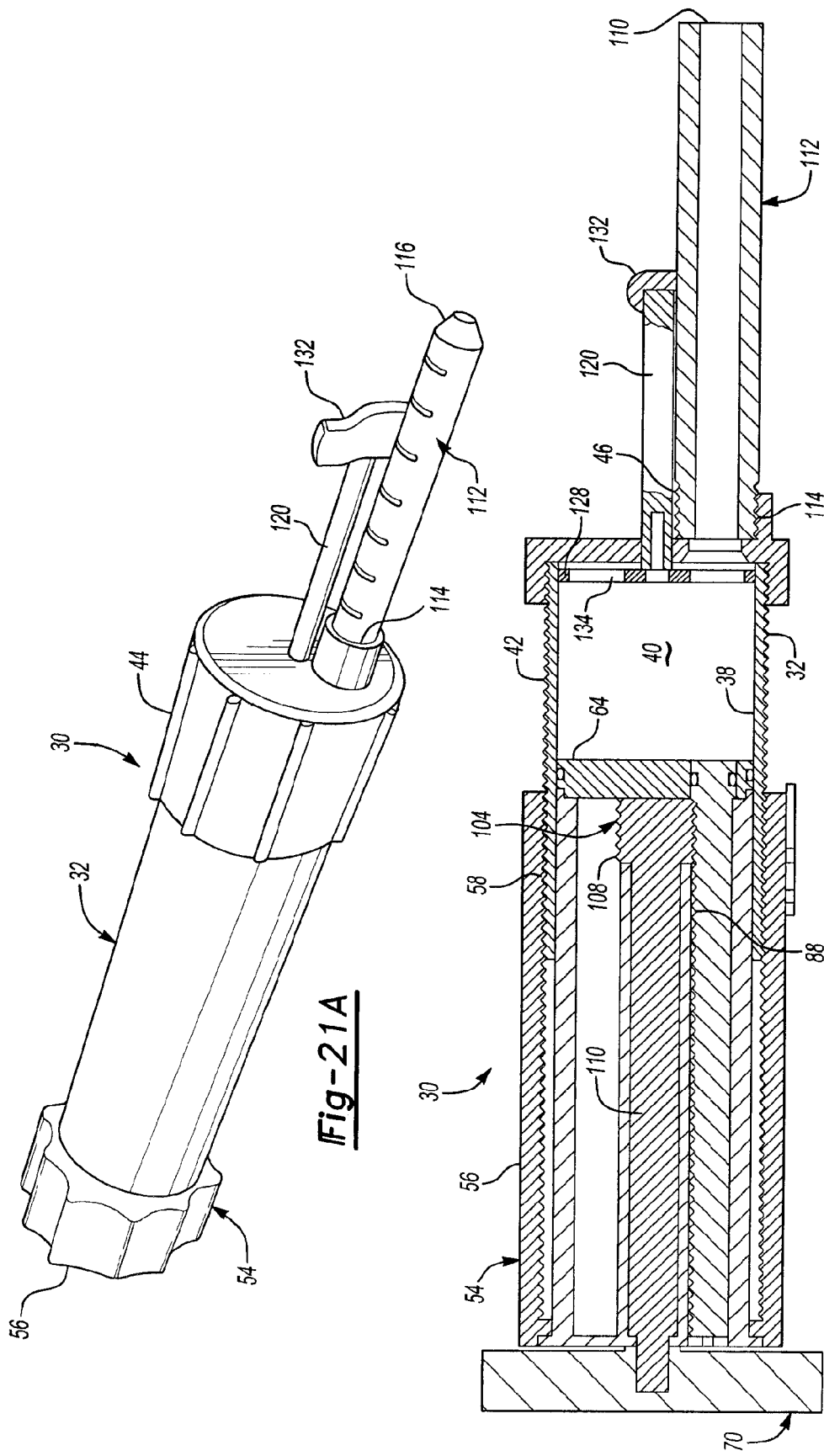
FIG. 21A is a perspective view of a sixth embodiment of a cement mixing and delivery device designed according to the present invention.
FIG. 21B is a cross-sectional view of the cement mixing and delivery device of FIG. 21A.

The subject invention may also be utilized with more than one delivery cartridge 112, as shown in FIG. 19. Multiple delivery cartridges 112 require a plurality of plungers 88 corresponding to each of the delivery cartridges 112. For instance, two plungers 88 may extend from the piston 64. The plungers 88 would be configured as described above with each plunger 88 engaging the second advancement mechanism 70. Therefore, actuation of the second advancement mechanism 70 advances both plungers 88. Alternately, the plungers 88 could have individual second advancement mechanisms such as the worm gear 108 or pinion gear 106 type of second advancement mechanisms 70. For percutaneous delivery, a flexible extension tube (not shown) is removable coupled to the open end 116. A needle having a handle (not shown) is coupled to the extension tube for injection through the skin and into the patient.

In one embodiment, the mixing and delivery assembly 30 also includes at least one indicator 118 disposed on the transfer mechanism 54 or rod 110 indicating an amount of the bone cement to be delivered into the patient upon rotation of the transfer mechanism 54 and the second advancement mechanism 70. For instance, the indicator 118 on the transfer mechanism 54 may represent a quarter of a turn. The quarter of a turn may further represent two cubic centimeters of bone cement to be delivered into the patient. The indicators allow medical personnel to easily and efficiently deliver predetermined amounts of the bone cement to the patient. In another embodiment, the delivery cartridge 112 includes markings indicative of the amount of bone cement delivered.

The assembly 30 of the subject invention can be used with a method of delivering the bone cement. The method includes the steps of filling the chamber 38 with the bone cement and sealing the chamber 38 by connecting the lid 44 to the proximal end 36. The preferred method includes disposing the liquid monomer and the powdered copolymer into the chamber and agitating the liquid monomer and the powdered copolymer to form the bone cement as described below. However, the subject invention is particularly useful with premixed bone cement. Once the mixed bone cement is in chamber 38, the next step is actuating the transfer mechanism 54 to advance the first advancement mechanism 68. Advancing the first advancement mechanism 68 includes advancing the piston 64 and the plunger 88 in unison for transferring the bone cement from the chamber 38 to the proximal end 36. In the preferred embodiment, actuation of the first advancement mechanism 68 begins by rotating the transfer mechanism 54. Rotation of the cap 56 causes the plurality of circumferential segments 60 to move along male threads 42. When the plurality of circumferential segments 60 reaches the annular recess 82, the first biasing device 84 forces the plurality of circumferential segments 60 radially inward and into the annular recess 82 thereby separating the plurality of circumferential segments 60 from the cap 56.

The method is then characterized by actuating the second advancement mechanism 70 and advancing the plunger 88 independently of the piston 64 to extend the plunger 88 beyond the piston 64 thereby delivering the bone cement into the patient. Specifically, in a preferred embodiment, once the plurality of circumferential segments 60 is recessed, the pin 94 engages the channel 66 in the mixing chamber 40 which fixes the position of the piston 64. Continued rotation of the cap 56 causes the plunger 88 to rotate within the piston 64 and extend therefrom. The cap 56 is rotated until the plunger 88 has moved into the delivery cartridge 112 to force the bone cement completely from the mixing chamber 40.

In alternate embodiments, the second advancement mechanism 70 has the rod 110 extending from the cartridge 32 and engaging the gear 104. After the piston 64 is locked in place, the rod 110 is rotated causing the plunger 88 to extend from the piston 64. Alternate aspects of the assembly 30, as described above, further include the steps of venting the chamber 38, removing gas particles from the chamber 38, and filtering the gas particles as the gas particles are removed from the chamber 38.

Figure 22:
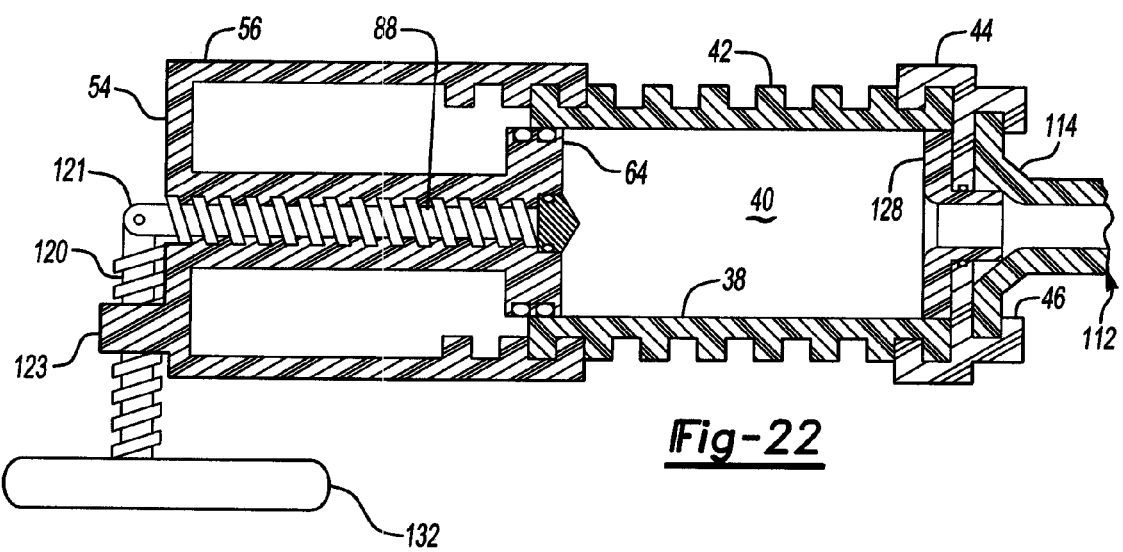
FIG. 22 is a cross-section view of a seventh embodiment of a cement mixing and delivery device designed according to the present invention.

The assembly 30 preferably is further used to mix the liquid monomer and powder copolymer in the mixing chamber 40, as shown in FIGS. 1-4. In the mixing phase, the assembly 30 includes a removable handle 120 extending through the aperture 46 and having a first end 122 and a second end 124 defining a hollow cavity 126 therebetween. Other embodiments may include the removable handle 120 extending through the cap 56. The removable handle 120 may also be used to move the plunger 88 through the aperture 46. One such removable handle 120 is illustrated in FIG. 22. The removable handle 120 includes a pivot 121 for engaging a cap stop 123. While in the transfer phase, the removable handle 120 pivots and is at a right angle with the plunger 88. The removable handle 120 can be used to rotate the cap 56 during this stage. During the delivery phase, the removable handle 120 is pivoted and coextensive with said plunger 88. Rotation of the removable handle 120 extends the plunger 88 from the piston 64.

Figure 10:
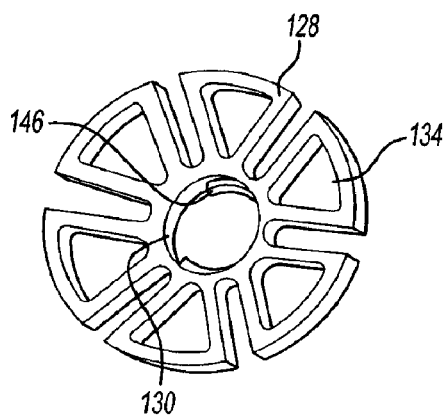
FIG. 10 is a perspective view of a mixing blade designed according to the present invention.
Figure 15:
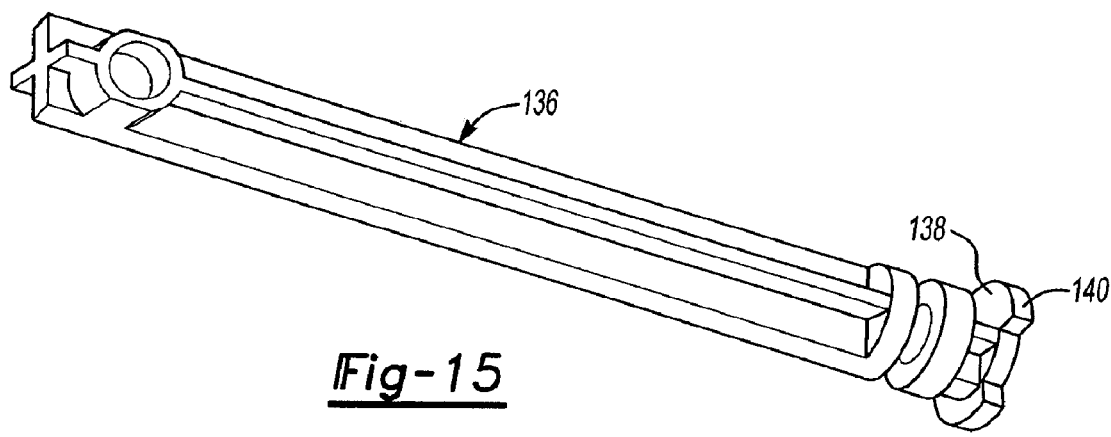
FIG. 15 is a perspective view of a shaft designed according to the present invention.

A mixing blade 128 (shown separately in FIG. 10) has a bore 130 for receiving the first end 122 of the removable handle 120. The second end 124 of the removable handle 120 allows a knob 132 to be attached for rotating and moving the mixing blade 128 through the mixing chamber 40. The mixing blade 128 may be any blade used for mixing, but is preferably a circular blade or a circular disc that is able to slide within the mixing chamber 40. The mixing blade 128 has a circumference which extends to the inner wall of the mixing chamber 40, while still allowing for movement of the mixing blade 128. The mixing blade 128 may further include slots 134 for increasing the efficiency of the mixing. A shaft 136 (shown separately in FIG. 15) is disposed within the hollow cavity 126 and has a blade attachment end 138 with projections 140 extending from the first end 122. A shaft seal 141 is disposed between the shaft 136 and the removable handle 120 for preventing cement from flowing therebetween.

A quick-release bayonet-type connector 142 is located between the mixing blade 128 and the shaft 136 such that the mixing blade 128 is releasably connected to the removable handle 120. A release button 144 engages the shaft 136 and is movable between a locked position and an unlocked position. The quick-release connector 142 further includes flanges 146 extending inward from the bore 130 of the mixing blade 128 and a pair of flange recesses 148 disposed within the first end 122 of the removable handle 120. In the unlocked position, the projections 140 are offset from the flange recesses 148 such that the flange 146 can be received by the flange recess 148. Movement of the release button 144 causes the shaft 136 to rotate while the removable handle 120 remains still. The shaft 136 rotates causing the projections 140 to engage the flanges 146 and force the flanges 146 into the flange recess 148. Once the release button 144 is in the locked position, the mixing blade 54 is locked to the removable handle 120. The removable handle 120 is manipulated manually or by a motor (not shown) to move the mixing blade 54 through the mixing chamber 40 and mix the cement components. The removable handle 120 is of sufficient length to extend the mixing blade 128 through the entire length of the mixing chamber 40 and rotate the mixing blade 128 to ensure complete mixing.

Figure 23:
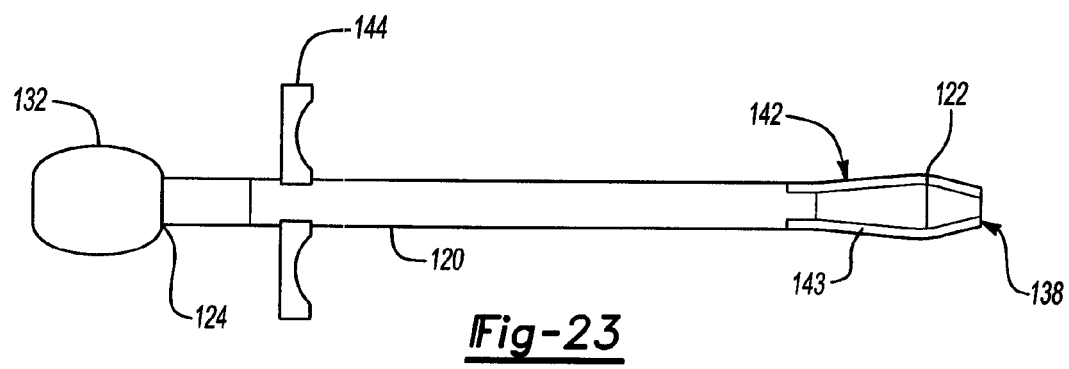
FIG. 23 is a perspective view of an alternate embodiment for a removable handle.

An alternate quick-release connector 142 is shown in FIG. 23. A collapsible ball 143 is connected to the first end 122 of the removable handle 120. When the release button 144 is in the unlocked position, the collapsible ball 143 is collapsed and can be inserted into the bore 130. The release button 143 is moved to the locked position and the collapsible ball 143 engages the bore 130 thereby locking the mixing blade 128 to the removable handle 120.

The assembly 30, as utilized in the mixing phase, includes a method of mixing the powdered copolymer and the liquid monomer to form the bone cement. The method includes the steps of disposing the powdered copolymer and the liquid monomer into the mixing chamber 40 and connecting the lid 44 to the proximal end 36 to seal the mixing chamber 40 having the mixing blade 128 disposed within the mixing chamber 40. Preferably, the removable handle 120 is inserted through the aperture 46 of the lid 44 while the lid 44 is not connected to the cartridge 32. However, the quick-release connector 142 allows for the mixing blade 128 to be initially within the mixing chamber 40 and the lid 44 attached when inserting the removable handle 120 through the aperture 46. Additionally, the two components may be added with the lid 44 already connected and the mixing blade 128 disposed within the mixing chamber 40. The removable handle 120 is manipulated moving the mixing blade 128 and agitating the powdered copolymer and the liquid monomer to form the bone cement. As the components are mixed together, a chemical reaction ensues, producing a gas that may be harmful if inhaled by the medical personnel. The vacuum is applied to the vent 48 to remove gas particles from the mixing chamber 40 preventing the gas from being inhaled. The removal of the gas also ensures that the bone cement will be formed without gas bubbles providing a stronger cement. Additionally, the filter 50 may be utilized for filtering the gas particles as the gas particles are being removed from the mixing chamber 40.

Once mixing is complete, the release button 144 is moved to the unlocked position thereby releasing the mixing blade 128 from the quick-release connector 142 such that the removable handle 120 is removable through the aperture 46 and the mixing blade 128 remains in the mixing chamber 40. When the release button 144 is moved to the unlocked position, the shaft 136 is rotated causing the projections 140 of the blade attachment end 138 to be offset from the flanges 146 of the bore 130. The removable handle 120 is then removed from the bore 130 of the mixing blade 128 and through the aperture 46. Since the mixing blade 128 is released without having to break the removable handle 120, the bone cement does not become contaminated with fragments FIGS. 20A & B illustrate another embodiment of the cement mixing and delivery assembly 30. The first advancement mechanism 54 is actuated by rotating the cap 56 to move the piston 64 through the mixing chamber 40 along the male threads 42. The assembly 30 allows the removable handle 120 to remain in the mixing chamber 40 while the second advancement mechanism 70 is operated. The second advancement mechanism 70 includes the plunger 88 extending through the removable handle 120 and through the mixing blade 128. The delivery cartridge 112 extends from the lid 44 while the plunger 88 and the removable handle 120 extend through the cap 56. The second advancement mechanism 70 is actuated by forcing the plunger 88 through the delivery cartridge 112 to deliver the bone cement by applying a force to the knob 132 of the removable handle 120. In this embodiment, the mixing blade 128 has tapered slots 134 to ensure better mixing and to assist in transferring the bone cement.

FIGS. 21A & B illustrate yet another embodiment of the cement mixing and delivery assembly 30. The mixing handle 120 and the delivery cartridge 112 both extend from the lid 44. The first advancement mechanism 54 is actuated by rotating the cap 56 to move the piston 64 through the mixing chamber 40 along the male threads 42. The second advancement mechanism 70 includes the rod 110 extending from the cartridge 32 and the gear 104 engaging the plunger 88. When the rod 110 is rotated, the plunger 88 moves linearly through the mixing blade 128 and through the delivery cartridge 112 to deliver the bone cement.

Obviously, many modifications and variations of the present invention are possible in light of the above teachings. The invention may be practiced otherwise than as specifically described within the scope of the appended claims.

What is claimed is:

1. A bone cement mixing and delivery system for delivering bone cement to a patient, said system comprising:

a container defining a chamber for receiving at least two separate components of the bone cement, said chamber having a first cross-sectional area;

a mixing device disposed in said chamber for mixing the at least two separate components of the bone cement to form a uniform bone cement mixture during a mixing phase;

a delivery device defining a cement flow path in fluid communication with said chamber to convey the bone cement mixture from said chamber to the patient, said cement flow path having a second cross-sectional area smaller than said first cross-sectional area;

a first transfer head positioned and dimensioned to advance through said chamber in a transfer phase and urge the bone cement mixture from said chamber to said cement flow path;

a second transfer head positioned and dimensioned to advance through said cement flow path in a delivery phase and urge the bone cement mixture from said cement flow path to the patient; and a transfer mechanism operatively coupled to said container and including a single drive member for actuating both of said transfer heads, said transfer mechanism further including first and second advancement mechanisms for transferring displacement of said drive member to said transfer heads so that when said drive member is displaced, said first advancement mechanism advances said first transfer head through said chamber to a stop position in the transfer phase and, automatically thereafter, said second advancement mechanism advances said second transfer head through said cement flow path in the delivery phase.

2. A system as set forth in claim 1 wherein said first transfer head includes a piston disposed in said chamber and said second transfer head includes a plunger moveable relative to said piston.

3. A system as set forth in claim 2 wherein said first advancement mechanism advances said piston and said plunger in unison to said stop position.

4. A system as set forth in claim 3 wherein said second advancement mechanism advances said plunger relative to said piston after said piston reaches said stop position.

5. A system as set forth in claim 2 wherein said container defines an aperture at a proximal end thereof and said delivery device is further defined as an injection tube having a first end connected to said aperture and extending to an open end wherein said plunger has a cross section permitting said plunger to extend through said aperture and into said injection tube.

6. A system as set forth in claim 2 wherein said drive member includes a cap rotatably supported by said container and rotatably displaced relative to said container to advance said transfer heads in the transfer phase and the delivery phase.

7. A system as set forth in claim 6 wherein said first advancement mechanism includes outer threads disposed on said container and inner threads supported by said cap, said inner threads engaging said outer threads upon rotation of said cap in the transfer phase to advance said piston and said plunger axially through the chamber.

8. A system as set forth in claim 7 wherein said second advancement mechanism includes coacting threads interconnecting said plunger and said piston for advancing said plunger axially relative to said piston in response to rotation of said cap when said piston is at said stop position.

9. A system as set forth in claim 8 including a disconnect system for disconnecting said inner threads from said outer threads such that rotation of said cap does not further advance said piston once said piston reaches said stop position after completion of the transfer phase and a pin system for rotationally locking said piston to said container once said piston reaches said stop position such that rotation of said cap advances said plunger relative to said piston in the delivery phase.

10. A method of mixing and delivering bone cement using a bone cement mixing and delivery system that includes a container defining a chamber, a mixing device disposed in the chamber, and a delivery device defining a cement flow path in fluid communication with the chamber to guide the bone cement from the chamber to a patient, said method comprising the steps of;

disposing at least two separate components of the bone cement in the chamber, mixing the at least two separate components of the bone cement disposed in the chamber with the mixing device to form a uniform bone cement mixture, transferring the bone cement mixture from the chamber to the cement flow path of the delivery device by advancing a first transfer head through the chamber to a stop position using a first advancement mechanism in a transfer phase, delivering the bone cement mixture from the cement flow path of the delivery device to the patient by advancing a second transfer head through the cement flow path using a second advancement mechanism in a delivery phase following the transfer phase, displacing a single drive member to operate both the first and second advancement mechanisms and advance the first and second transfer heads, and automatically switching from the transfer phase in which the first transfer head is advanced through the chamber to the delivery phase in which the second transfer head is advanced through the cement flow path in response to the first transfer head reaching the stop position.

11. A method as set forth in claim 10 wherein advancing the first transfer head includes advancing a piston and a plunger in unison within the chamber in the transfer phase.

12. A method as set forth in claim 11 wherein advancing the second transfer head includes advancing the plunger independently of the piston to extend the plunger beyond the piston in the delivery phase.

13. A method as set forth in claim 10 including rotating the drive member about an operational axis to advance the first and second transfer heads along the operational axis during the transfer and delivery phases.

* * * * *